(12) United States Patent
Molter et al.

(10) Patent No.: US 10,830,744 B2
(45) Date of Patent: Nov. 10, 2020

(54) HYDROGEN MONITORING AND DELIVERY COMPONENTS AND METHODS

(71) Applicants: Skyre, Inc., East Hartford, CT (US); University of Connecticut, Farmington, CT (US)

(72) Inventors: Trent M. Molter, Glastonbury, CT (US); Ugur Pasaogullari, Glastonbury, CT (US); Leonard J. Bonville, Marlborough, CT (US); Charles Banas, Norwich, CT (US); Gregory Hesler, Woodstock, CT (US)

(73) Assignees: SKYRE, INC., East Hartford, CT (US); UNIVERSITY OF CONNECTICUT, Farmington, CT (US)

( * ) Notice: Subject to any disclaimer, the term of this patent is extended or adjusted under 35 U.S.C. 154(b) by 184 days.

(21) Appl. No.: 16/000,118

(22) Filed: Jun. 5, 2018

(65) Prior Publication Data
US 2018/0372701 A1    Dec. 27, 2018

Related U.S. Application Data

(60) Provisional application No. 62/515,970, filed on Jun. 6, 2017.

(51) Int. Cl.
*G01N 33/00* (2006.01)
*G01N 27/407* (2006.01)
(Continued)

(52) U.S. Cl.
CPC ....... *G01N 33/005* (2013.01); *G01N 27/4071* (2013.01); *G01N 27/4074* (2013.01); *G01N 33/007* (2013.01); *G01N 27/301* (2013.01); *G01N 27/304* (2013.01); *G01N 27/333* (2013.01); *G01N 33/004* (2013.01); *G01N 33/0044* (2013.01); *G01N 2033/0072* (2013.01)

(58) Field of Classification Search
CPC .............. G01N 27/307; G01N 27/333; G01N 27/4071; G01N 27/4074; G01N 33/0009; G01N 33/0027; G01N 33/005; G01N 2033/0072; G01N 33/004
USPC .............................................. 73/31.05, 61.41
See application file for complete search history.

(56) References Cited

U.S. PATENT DOCUMENTS 6,063,516 A   5/2000  Grot et al.
7,150,932 B1  12/2006 Hofler et al.
(Continued)

OTHER PUBLICATIONS

Butterworth, S., "On the Theory of Filter Amplifiers," Experimental Wireless & The Wireless Engineer; Oct. 1930, pp. 536-541.
(Continued)

*Primary Examiner* — Benjamin R Schmitt
(74) *Attorney, Agent, or Firm* — Cantor Colburn LLP

(57) ABSTRACT

In an embodiment, a hydrogen monitoring system comprises a plurality of sensing elements that individually comprise a working electrode, a counter electrode, an insulating layer located in between the working electrode and the counter electrode, a catalyst located on an end of both the working electrode and the counter electrode, an electrolyte located on the end of the sensing elements on both the working electrode and the counter electrode, between the working electrode and the counter electrode, and in contact with the catalyst, and an electrical circuit located on an opposite end of the sensing element that connects the working electrode and the counter electrode.

20 Claims, 6 Drawing Sheets

(51) Int. Cl.
*G01N 27/30* (2006.01)
*G01N 27/333* (2006.01)

(56) References Cited

U.S. PATENT DOCUMENTS

| | | | |
|---|---|---|---|
| 2002/0187075 | A1 | 12/2002 | Nadanami et al. |
| 2008/0005965 | A1 | 1/2008 | Speranza |
| 2014/0127599 | A1 | 5/2014 | Kachi |
| 2015/0346140 | A1 | 12/2015 | Kirk et al. |

OTHER PUBLICATIONS

Invitation of Pay Additional Fee, International Application No. PCT/US2018/36006; International Filing Date: Jun. 5, 2018; dated Aug. 10, 2018; 2 pages.

Sethuraman et al., "Analysis of Sulfur Poisoning on a PEM Fuel Cell Electrode," Electrochimica Acta; 2010, pp. 5683-5694, vol. 55, Issue 20.

Wang et al., "An experimental overview of the effects of hydrogen impurities on polymer electrolyte membrane fuel cell performance," International Journal of Hydrogen Energy; 2014, pp. 19701-19713, 39.

Zhang et al., "Contamination of Membrane-Electrode Assemblies by Ammonia in Polymer Electrolyte Fuel Cells," ECS Transactions; 2009, pp. 1565-1574, 25 (1).

Zhang et al., "Influence of ammonia on membrane-electrode assemblies in polymer electrolyte fuel cells," International Journal of Hydrogen Energy; 2009, pp. 9188-9194, 34.

Zhang et al., "Influence of Formic Acid Impurity on Proton Exchange Membrane Fuel Cell Performance," Journal of The Electrochemical Society; 2010, pp. B409-B414, 157(3).

International Search Report; International Application No. PCT/US18/36006; International Filing Date: Jun. 5, 2018; dated Oct. 16, 2018; 6 pages.

Written Opinion; International Application No. PCT/USI8/36006; International Filing Date: Jun. 5, 2018; dated Oct. 16, 2018; 13 pages.

HYDROGEN MONITORING AND DELIVERY COMPONENTS AND METHODS

CROSS-REFERENCE TO RELATED APPLICATION

This application claims the benefit of U.S. Provisional Patent Application Ser. No. 62/515,970 filed Jun. 6, 2017. The related application is incorporated herein in its entirety by reference.

BACKGROUND

The subject matter disclosed herein relates to hydrogen monitoring and delivery.

Air and fuel quality has been a major issue for many hydrogen fuel cell deployments. In particular, fuel quality is among the issues that has been shown to affect robustness, reliability, and durability of power production on board fuel cell vehicles. Hydrogen fuel can contain various contaminants at different levels. For example, much of the hydrogen on the commercial market is produced by chemical process reforming of methane, and various contaminants can be present in the methane source (i.e., natural gas) or various contaminants can be introduced during chemical processing. Even for hydrogen produced by electrolysis or other means that may avoid the contaminants contained in natural gas, contaminants can be introduced to hydrogen fuel during transportation, storage, or dispensing. Some contaminants such as carbon monoxide can have a deleterious effect on fuel cell performance, and significant effort has been exerted to develop high purity sources of hydrogen with controlled levels of contaminants.

However, capabilities for testing hydrogen to ensure that purity targets are met have largely been limited to laboratory practice in which samples are required to be obtained (e.g., according to ASTM D7606-11) and usually sent away to a laboratory, where specially skilled personnel perform analytical chemistry experiments on specialized equipment. Such laboratory analyses can be expensive, and their inability to provide results in real-time can allow for significant quantities of contaminated hydrogen to be dispensed before the contamination is identified. Accordingly, there remains a need for further developments in the field of hydrogen monitoring and delivery.

BRIEF SUMMARY OF THE DISCLOSURE

Disclosed herein is a hydrogen monitoring system and methods of using the same.

In an embodiment, a hydrogen monitoring system comprises a plurality of sensing elements that individually comprise a working electrode, a counter electrode, an insulating layer located in between the working electrode and the counter electrode, a catalyst located on an end of both the working electrode and the counter electrode, an electrolyte located on the end of the sensing elements on both the working electrode and the counter electrode, between the working electrode and the counter electrode, and in contact with the catalyst, and an electrical circuit located on an opposite end of the sensing element that connects the working electrode and the counter electrode.

A hydrogen delivery system can comprise a hydrogen source, an inlet fluid flow path from the hydrogen source to the hydrogen monitoring system, and an outlet fluid flow path from the hydrogen monitoring system to an outlet.

A method of determining a level of a contaminant in a hydrogen gas using the hydrogen delivery system can comprise flowing the hydrogen gas from the hydrogen source along the inlet fluid flow path, past the plurality of sensing elements, and along the outlet fluid path to the outlet; measuring a data obtained from the electrical circuit and reading the data via a software program; manipulating the data to provide a manipulated data; optionally applying a filter or a noise reduction algorithm; comparing the manipulated data to a pre-determined contaminant threshold; determining if the manipulated data is greater than, less than, or equal to the pre-determined contaminant threshold and providing a decision label based on the determining; and providing an output data comprising the decision label.

The above described and other features are exemplified by the following figures, detailed description, and claims.

BRIEF DESCRIPTION OF THE DRAWINGS

The Figures herein may utilize the same numbering as from other Figures without repeating the original description, and unless otherwise explicitly stated, such repeated numbering shall have the same meaning in all Figures. The Figures provide non-limiting embodiments of the present disclosure.

DETAILED DESCRIPTION

According to some embodiments, a hydrogen monitoring system includes a plurality of electrochemical cells that individually comprise a working electrode, a counter electrode, and an electrolyte between the working electrode and the counter electrode(s). In some embodiments, any of the electrochemical cells can include an additional counter electrode that can be utilized, for example, as a reference electrode with the proper catalyst. In some embodiments, the plurality of electrochemical cells can be disposed on a plurality of sensing elements (e.g., one cell per sensing element). In some embodiments, multiple cells can be disposed on any of the electrochemical sensing elements such that the electrochemical sensing element can include additional counter electrodes and/or additional working electrodes so that the electrochemical sensing element can include a cell with two electrodes (working and counter electrodes), a cell with three electrodes (working electrode, counter electrode, and pseudo-reference electrode), or multiple cells with two and/or three electrodes (multiple working electrodes, with concomitant working/counter/pseudo-reference electrodes). As used herein, the term "electrode" is not limited to any particular type of structure, and includes any electroactive surface that is part of an electrochemical sensing element.

In some embodiments, a hydrogen delivery system includes a hydrogen source, a fluid flow path from the hydrogen source to a hydrogen monitoring system including a plurality of electrochemical cells or sensing elements as described above, and a fluid flow path from the hydrogen monitoring system to an outlet.

In some embodiments, different electrochemical cells among the plurality of electrochemical cells or sensing element can comprise different materials, such as different working or counter electrode materials, or different electrolyte materials, or is operated at different conditions. Such differences can promote the capability of the different electrochemical cells of the hydrogen monitoring or delivery system to test for different contaminants.

Figure 1A:
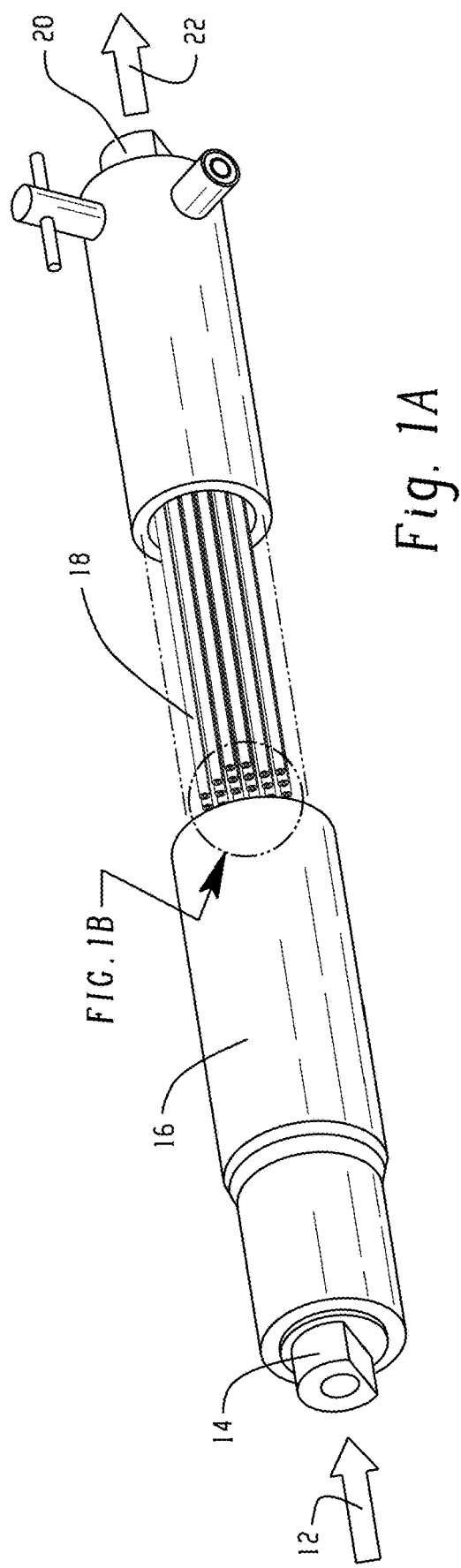
FIG. 1A is a schematic depiction of an example embodiment of a multi-sensing element hydrogen contaminant detector comprising a plurality of electrochemical cells and FIG. 1B is a schematic depiction of an enlarged area of the plurality of electrochemical sensing elements of FIG. 1A.
Figure 1B:
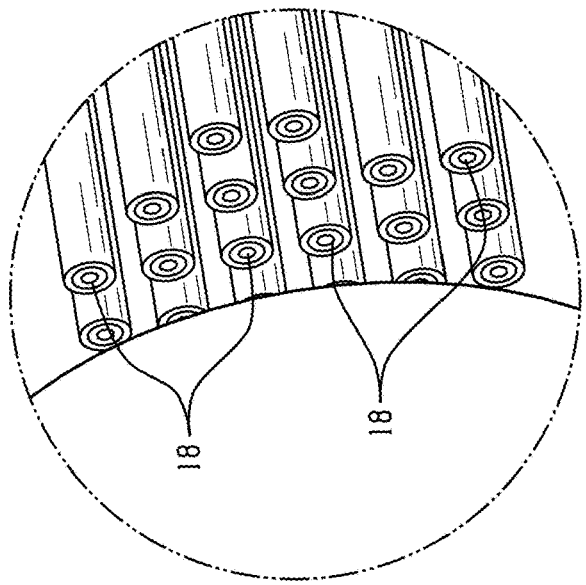

An example embodiment of a hydrogen delivery or monitoring assembly is shown schematically in FIG. 1A and FIG. 1B. As shown in FIG. 1A and FIG. 1B, hydrogen source 12 delivers hydrogen to an inlet 14 of a tubular housing 16. The fluid hydrogen is directed along a flow path inside the housing to a plurality of electrochemical sensing elements 18, from which the hydrogen proceeds to an outlet 20 of the housing 16, and to a hydrogen dispenser 22. The housing 16 can be integrated into a hydrogen delivery system at various locations, including but not limited to upstream of and proximate to a dispensing connector for connection to a vehicle fuel storage tank, as part of a breakaway connector, or between a cold block and a compressor for the hydrogen storage. The particular configuration of the sensing elements can be chosen on factors such as target packaging size and fluid flow configurations. For example, a common electrochemical sensing element configuration can be used comprising a layer of film of electrolyte sandwiched in between an electrode/current collector on opposite film surfaces.

Figure 2:
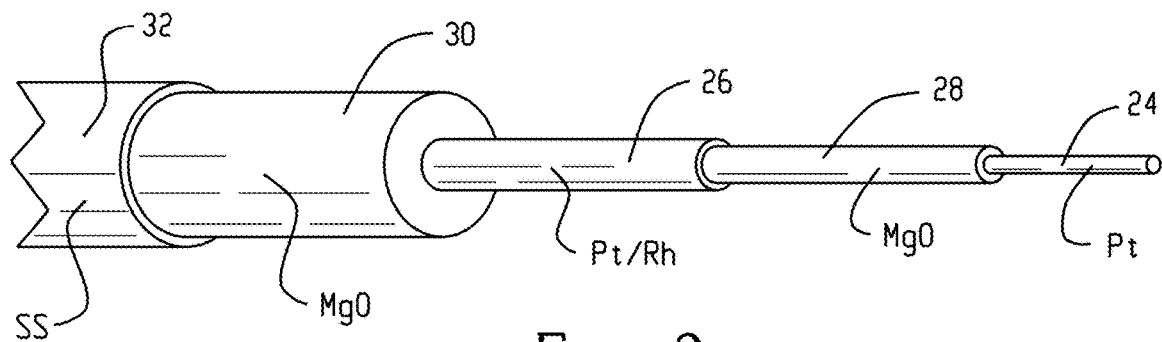
FIG. 2 is a schematic depiction of an example embodiment of a cutaway view of a sensing element.
Figure 3A:
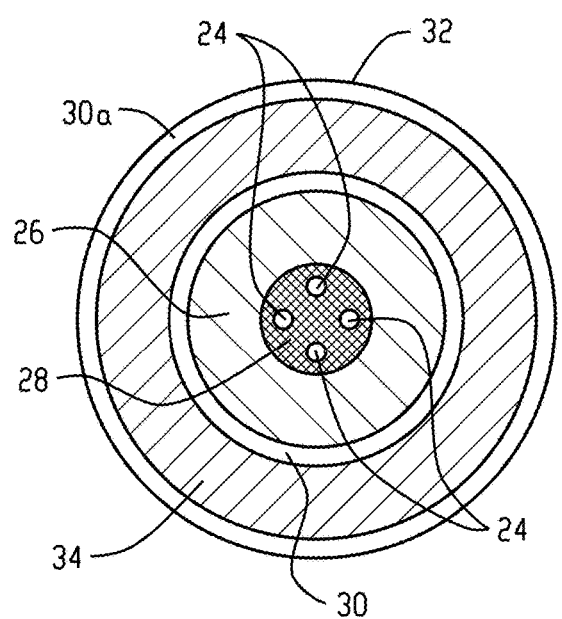
FIGS. 3A and 3B are schematic depictions of end and side cross-sectional views, respectively, of another example embodiment of a sensing element.
Figure 3B:
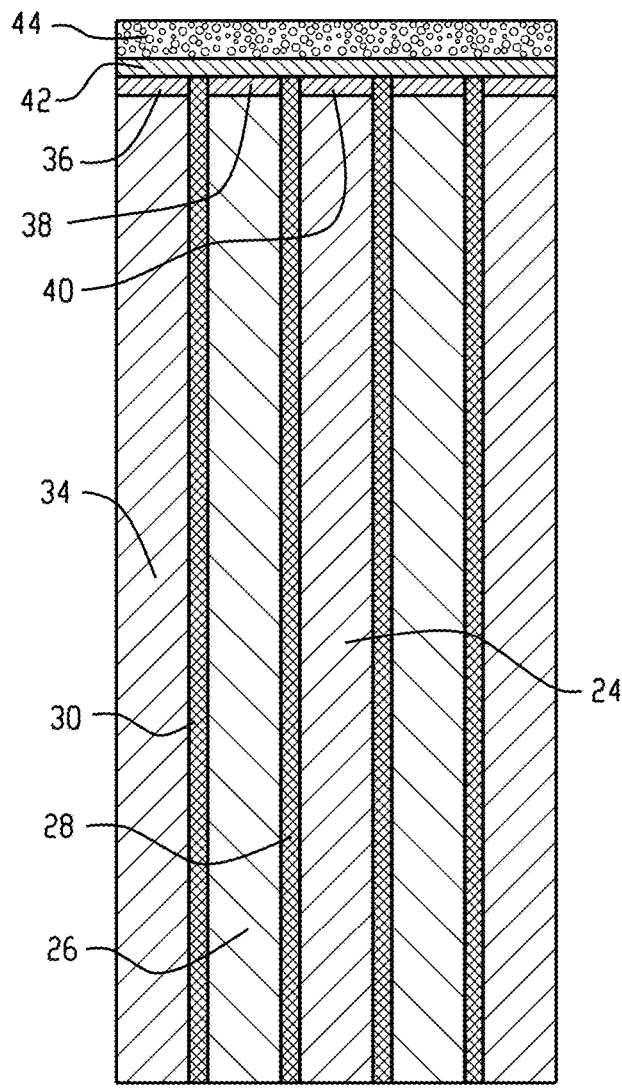

In some embodiments, such as shown in FIGS. 1-3, the sensing element can be configured as a linearly-extending probe configured to operate in a pressurized gas environment, which can utilize adaptations for attachment and sealing to system components such as are used for thermocouples, spark plugs, engine exhaust oxygen sensors, or mounted solid state microchip (e.g., MOS) sensors. Examples of one configuration type of sensing element 18 are schematically shown in FIGS. 2, 3A, and 3B, configured as a multilayered axially extending cylindrical member. As shown in a layered cut-away view in FIG. 2, an electrochemical sensing element includes a working electrode 24 and a first counter electrode 26, isolated by insulating layers 28 and 30 and covered by a sheath 32. It is noted that FIG. 3A illustrates that the central electrode can comprise more than one working electrode 24, for example, 2 to 10, or 2 to 4 working electrodes, where it is noted that this central electrode could likewise comprise more than one counter electrode 26. It is noted that the term 'central electrode' merely refers to the electrode being located within an innermost insulating layer. These multiple central electrodes can be individually insulated from each other. While the figures illustrate the central electrode to be working electrode 24 and the neighboring electrode to be a first counter electrode 26, electrode 24 could be the counter electrode and electrode 26 could be the working electrode 24. Likewise, while the core of the sensing elements is generally referred to herein as comprising an electrode, the core can be an insulating layer. Sheath 32 can be for protective purposes only (e.g., not connected to the electrolytic circuit) or it can serve as a counter electrode, in which case there would be additional housing to protect the sensing element.

The electrodes 24 and 26 shown in FIG. 2 can be formed from any type of conductor, with a designated catalyst (e.g., Pt/Rh or Pt) deposited at the tip as shown in FIG. 3B. The electrodes 24, 26, and 34 can each independently comprise at least one of gold, platinum, palladium, copper, iridium, rhodium, tantalum, titanium, niobium, nickel, carbon, or silver. The electrodes 24, 26, and 34 can each independently comprise at least one of gold, platinum, palladium, copper, rhodium, nickel, or silver. The electrodes 24, 26, and 34 can each independently comprise platinum or an alloy thereof. For example, in some embodiments the working electrode 24 can be a metal wire (for example, a metal wire comprising at least one of gold or platinum, e.g., a 28 gauge gold wire or a $10/1000"$ platinum wire). The electrode 24 can have a diameter of 10 micrometers to 1 millimeters (mm), or 100 micrometers to 1 mm, or 0.1 to 0.5 mm. The electrode 26 and electrode 34 can independently have a thickness as defined by an outer radius minus an inner radius of 10 micrometers to 1 mm, or 100 micrometers to 1 mm, or 0.1 to 0.5 mm. Other example dimensions and materials are shown in FIGS. 3A and 3B. FIGS. 3A and 3B show end and side views of an example electrochemical sensing element that includes a second counter electrode 34 and another non-conductive layer 30a. FIG. 3A illustrates an embodiment where the central electrode 24 comprises four separate electrodes 24, whereas FIG. 3B illustrates an embodiment where the central electrode 24 comprises a single electrode 24.

The insulating layers 28 and 30 can each independently comprise an electrically insulating material. The electrically insulating material is not particularly limited and can, for example, comprise at least one of a metal oxide, for example, at least one of a metal oxide (for example, aluminum oxide, chromium oxide, magnesium oxide, silicon oxide, titanium oxide, zinc oxide, or zirconium oxide), or a polymeric material (for example, a fluoropolymer such as polytetrafluoroethylene). The insulating layers 28 and 30 can each independently have a thickness as defined by an outer radius minus an inner radius of 10 micrometers to 5 mm; 10 micrometers to 3 mm, or 20 micrometers to 0.5 mm. The outer diameter of the sensing element minus a sheath can be 1 to 10 mm, 1 to 5 mm, or 0.5 to 1.5 mm A length of the sensing element can be 1 to 260 mm, or 50 to 130 mm. An example of a sensing element having a length of 3 inches is illustrated in FIG. 3B.

In some embodiments, one of the counter electrodes 26 and 34 can function as a reference electrode. In some embodiments, the counter electrode 34 can function as a reference electrode. It is noted, however, that the relative positions of the electrodes shown in FIGS. 2 and 3 represent an example embodiment, and any of the depicted electrode positions can be transposed with any of the other positions (e.g., the working electrode could be the radially outermost electrode instead of at the center as shown. As shown in FIG. 3B, a catalyst 36 is disposed on the tip of the working electrode 24, a catalyst 38 is disposed on the tip of the counter electrode 26, and a catalyst 40 is disposed on the tip of the counter electrode 34. An electrolyte 42 and a porous support layer 44 are shown disposed over the catalyzed electrode surfaces at the tip of the sensing element. An example of a porous support layer is a glass frit. In the example embodiments of FIGS. 2-3, the electrolyte 42 is configured as an ion bridge structure disposed across the electrodes at the tip of the sensing elements with both electrodes on the same side of an electrolyte layer; however, other structures could be used in which an electrolyte material is sandwiched between electrodes.

Suitable catalytic materials for the electrodes include, but are not limited to, platinum, palladium, rhodium, carbon, gold, tantalum, tungsten, ruthenium, iridium, titanium, osmium, alloys thereof, and the like, as well as combinations of the foregoing materials. In some embodiments, the catalyst comprises discrete catalytic particles. The catalyst can be supported (e.g., on carbon particles applied to the electrodes) or unsupported (e.g., applied directly to the electrode). Deposition of the catalyst onto the electrodes can be by any method including, but not limited to, jet printing, spraying, dipping, painting, imbibing, vapor deposition, electroplating, combinations of the foregoing methods, and the like. In some embodiments, the catalyst can be applied as particles dispersed in an ink containing a binder. In some embodiments, the catalyst can be directly applied such as by physical vapor deposition or electroplating.

Various types of materials can be utilized as the electrolyte. The electrolyte can provide a medium for passage of protons, hydroxyl ions, or other positively or negatively charged ions. More specifically, in some embodiments, the electrolyte can provide a medium for passage of protons. In some embodiments, the electrolyte can provide a medium for passage of hydroxyl ions. In some embodiments, the electrolyte can provide a medium for passage of other positively or negatively charged ions such as oxygen ions ($O^{2-}$), carbonate ions ($CO_3^{2-}$), sodium ions (Nat), or chloride ions ($Cl^-$). Examples of ion-conducting materials for the electrolyte can include perchloric acid, phosphoric acid, acid gels, ionic liquids, or ion-conducting polymer such as proton conducting ionomers and ion exchange resins. Ionic liquids are defined as salts that are in a liquid state at the relevant operating temperature of the sensor. Examples of ionic liquids include ionic species comprising 1-alkyl-3-methyl-imidazolium cations with any common anion. Ion-exchange resins useful as proton conducting materials include hydrocarbon- and fluorocarbon-type resins. Fluorocarbon-type resins typically exhibit excellent resistance to oxidation by halogen, strong acids, and bases. One family of fluorocarbon-type resins having sulfonic acid group functionality is NAFION resins (commercially available from E. I. du Pont de Nemours and Company, Wilmington, Del.). Combinations of ion-conducting materials can be used, such as an ionomer film cast from a solvent solution comprising NAFION and an acid such as phosphoric acid. In some embodiments, the electrolyte or ion bridge can comprise an ionically non-conductive framework, skeleton, or matrix structure with an ionic-conducting electrolyte material retained in the non-conductive framework, skeleton, or matrix structure. For example, in some embodiments, the electrolyte can comprise a porous hydrophobic polymer matrix (e.g., 0.5 mil thickness) that is saturated with a solvent solution comprising an ionomer such as NAFION as electrolyte, followed by evaporation of the solvent to produce a porous electrolyte structure. In some embodiments, a polymer matrix comprising both hydrophobic pores and hydrophilic pores can be used, with the hydrophobic pores available for gas transport and hydrophilic pores available for the electrolyte.

The various components of the structures shown in FIGS. 2 and 3 can be formed or fabricated in place, or the structure can be built up from pre-fabricated component, or combinations of techniques. For example, the insulating layers 28, 28', and 28" can be pre-formed tubes that are packed/assembled with the electrodes and other components, or they can be fabricated in place, for example by applying a ceramic powder or powder slurry followed by sintering.

Although wet electrolytes are not excluded from this disclosure, ion-conducting materials that rely on the presence of water can be subject to evaporation, so in some embodiments, the electrolyte can be anhydrous. For embodiments such as FIGS. 2-3, in which an ion bridge is interposed between the gas being monitored and the catalyzed electrodes, the ion bridge should, in addition to conducting ions, allow for mass transport of both hydrogen and contaminant molecules to the catalyzed electrode surface. In some embodiments, the ion bridge can include a microporous or mesoporous structure, or other pores or openings that can promote mass transport of gas. The size of such pores/openings can range from tens of nanometers (e.g., a porous NAFION film) to tens of micrometers (e.g., laser-drilled perforations. Electrolyte elements can be applied as an ink or a cast film in a solvent by dip coating, spray coating, spin coating, ink jet coating, etc. The ink or casting formulations can include non-conducting supports such as metal oxide or ionomer particles, as well as binders and other conventional ink or film components. Alternatively, a film such as an ionomer film can be pre-formed and then applied to (e.g., wrapped) around the sensor tip, optionally with the presence of an ionomer solution or ionic liquid to promote contact with the electrodes. Pore formers or scaffold materials can be included to provide porosity. Post application processing such as laser drilling, forming, or hot pressing can also be applied to the deposited material, with hole patterns optimized to provide for gas transport and ionic conductivity.

Some specific examples of additional materials for the electrolyte are set forth below in Table 1:

TABLE 1

| Name of | Description |
|---|---|
| PBI-IL ([EMIM][TFSI]) | Polybenzimidazole (PBI) filled with 1-ethyl-3-methylimidazolium |
| PBI-IL (HMI-TF) | Dissolved PBI synthesized with 1-hexyl-3-methylimidazolium |
| PBI-PWA-PA | PBI synthesized with phosphotunstic acid; doped with phosphoric acid |
| PBI-BS | Butylsulfonated PBI |
| sAB-PBI | sulfonated poly(2,5-benzimidazole) |
| PBI-P4VP | PBI with poly(4-vinylpyridine) |
| PFSA-IL(TEATF) | Nation doped with triethylammonium-triflate |
| ETFE-SA | sulfonated poly(ethylene-alt-tetrafluoroethylene); |

TABLE 1-continued

| Name of | Description |
|---|---|
| sPEEK+ | sulfonated poly(ether ether ketone) |
| sPPZ+ | sulfonated poly(phosphazene) |
| PVA-PWA-PA | Poly vinyl alcohol synthesized with Phosphotunstic acid, doped with |
| PEO-MDP | Polyethylene oxide with acid moieties monododecylphosphate (or PWA) |
| PTMO-PWA | poly(tetramethylene oxide) with phosphotunstic acid (orMDP) |
| PBI-[Cmim][NTf2] | PBI filled with1-ethyl-3-methylimidazolium |
| PBI-[Cmim][OTf] | PBI filled with1-ethyl-3-methylimidazolium trifluoromethylsulfonate |
| PBI-[Cmim][BF4] | PBI filled with1-ethyl-3-methylimidazolium tetrafluoroborate |
| PBI-[Cmim]]PF4] | PBI filled with1-ethyl-3-methylimidazolium tetrafluorophosphate |
| PBI-[Cmim][FAP] | PBI filled with1-ethyl-3-methylimidazolium tris(perfluoroethyl)triphosphate |
| PBI-[Cmim][***] pH | Same as above, pH adjusted with ~100% phosphoric acid |
| PBI-[Cmim][***] | Mixtures of at least one of the above |

In some embodiments, the electrochemical contaminant detector can be configured to operate over a wide range of gas pressures. In some embodiments, the operating pressure can be in a range having a lower end of greater than zero (e.g., 1 pounds per square inch (psi)) and an upper end of 15,000 psi. Specialized detectors can be designed for target pressure ranges. For example, in some embodiments, a hydrogen contaminant detector can be configured to operate in a pressure range of 8000 psi to 12,000 psi for hydrogen fueling for fuel cell vehicles. The above upper and lower range endpoints can be independently combined to form a number of different ranges, and each possible combination of endpoints is hereby explicitly disclosed. In some embodiments, the sealed cylindrical electrochemical cell structure of FIGS. 2-3 can provide a structure capable of operating at high pressures. In some embodiments, fittings on the hydrogen monitoring assembly of FIG. 1 can be any commercially-available high-pressure fluids fitting. Multiple fluids streams can be processed independently using machined, cast or welded manifold blocks.

Figure 4:
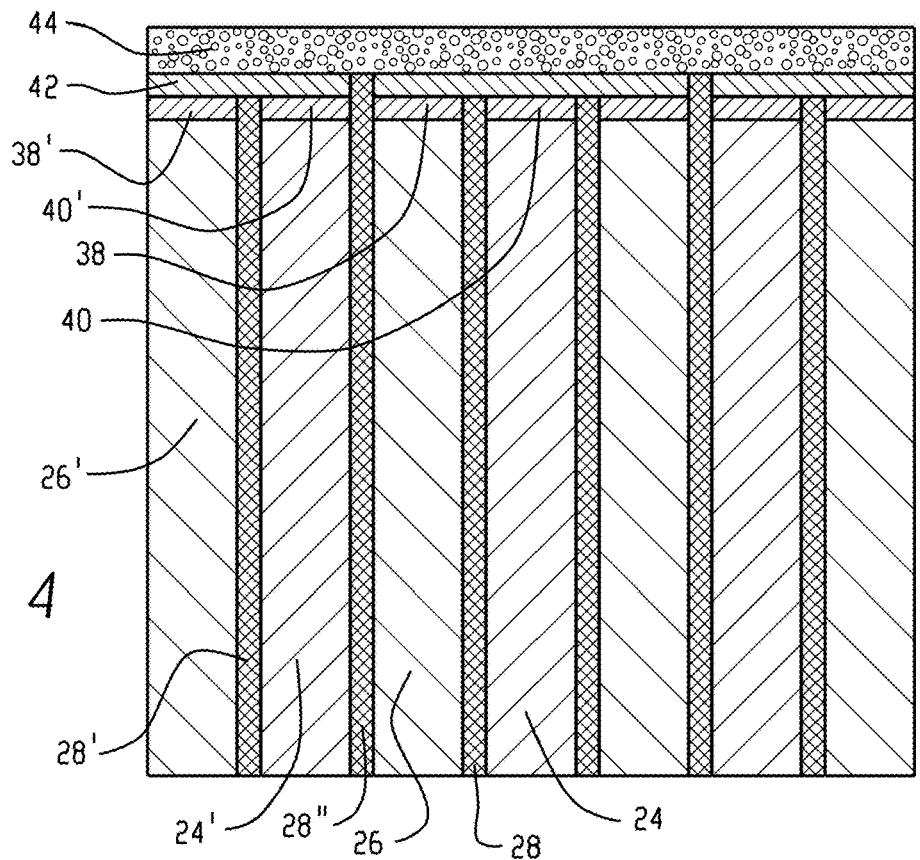
FIG. 4 is a schematic depiction of a side cross-sectional view of an example embodiment of a multi-cell sensing element.

As mentioned above, the hydrogen contaminant detection system/assembly can include a plurality of electrochemical cells or sensing elements. FIG. 1 depicts an example embodiment in which a plurality of cylindrical configured electrochemical sensing elements 18 are disposed in a housing 16. Other configurations can also be used. For example, the structures of FIGS. 2-3 can be adapted to include as many as 12 or more conductors instead of the 2 conductors (electrodes 24 and 26) shown in FIG. 2, allowing for multiple electrochemical cells, with additional non-conductive layers similar to layers 28 and 30 extending axially through the electrolyte at the tip of the structure to isolate the cells from each other. Other configurations or manufacturing techniques may allow for even greater numbers of conductors on a single component. An example embodiment of a sensing element comprising multiple conductors and cells is schematically shown in a cross-sectional side view in FIG. 4. As shown in FIG. 4, the example embodiment of an electrochemical sensing element includes a first cell that comprises working electrode 24 with catalyst 40 and counter electrode 26 separated by insulating layer 28, and a second cell that comprises working electrode 24' and counter electrode 26' separated by insulating layer 28'. Insulating layer 28" extends through the electrolyte 42 to isolate the electrochemical cells from each other. The embodiment in FIG. 4 represents one example embodiment, and other variations can be implemented. For example, a sensing element can include multiple cells in which each cell has its own working electrode, but multiple cells can share a common counter electrode.

In operation, the electrochemical sensor operates in a fashion analogous to a hydrogen pump cell, where hydrogen supplied to the working electrode of the sensing element (after diffusing, in the case of the structures of FIGS. 2 and 3 through the glass frit 44 and the electrolyte 42) is oxidized according to the formula: $H_2 \rightarrow 2H^+ + 2e^-$. The rate of this reaction is dependent on the fractional coverage of the surface with absorbed H atoms. Some contaminants like CO are preferentially absorbed at the electrode compared to $H_2$, so even at low concentrations, the presence of CO decreases the H coverage and results in increased overpotential (under constant current) or decreased current (under constant potential). Protons produced at the working electrode are transported across (i.e., through) the electrolyte to the counter electrode, where the protons are reduced to hydrogen according to the formula: $2H^+ + 2e^+ \rightarrow H_2$. As the counter electrodes in the sensing element have a much higher surface area (e.g., at least 3 to 4 orders of magnitude higher), the change in the counter electrode overpotential is negligible. Electrons released at the working electrode 24 produce an electrical signal through a circuit (FIG. 5) connecting the working electrode 24 and the counter electrode 26, and electrons are provided at the counter electrode 26 for the reducing reaction.

In some embodiments, the catalyst on the electrodes can be configured to promote the detection of targeted species. For example, in some embodiments, the catalyst on the working electrode can be a relatively low surface area catalyst, which can be achieved in some embodiments by applying a thin layer of catalyst material by any number of means including ink dipping or spraying, vapor deposition or electroplating to the surface of a polished metal (e.g., a platinum-tipped gold wire for the working electrode 24) or by fabricating the electrode from a catalytic metal (e.g., a platinum wire for the working electrode 24). In some embodiments, the working and counter electrode catalysts can have a cross-sectional surface areas in a range with a low end of 0.01 millimeters squared ($mm^2$) (e.g., a 0.005" (inch) diameter polished Pt wire), and an upper end of 10,000 $mm^2$ (e.g., a ⅛" metal sheath coated at the tip with high-surface area Pt on carbon support at about 0.5 milligrams per centimeter squared ($mg/cm^2$) loading).

In some embodiments, a relatively low surface area catalyst (e.g., a polished or plated metal catalyst surface) for the working electrode can provide a technical effect of promoting a rapid response of the sensor to changes in the gas such as a spike in a contaminant level. In such embodiments, the catalyst on the counter electrode(s) can also have a low surface area, or it can have a higher surface area. In some embodiments, the catalyst on the counter electrode(s) can be a relatively high surface area catalyst, such as a carbon-supported catalyst. A relatively high surface area catalyst can provide a technical effect of promoting a slow response of the sensor to changes in the gas such as a spike in a contaminant level, which can allow for the counter electrode to operate as a pseudo-reference electrode without the normal requirement of exposing the reference electrode to uncontaminated gas. A slow response by one of the counter electrodes can allow for the working electrode to provide a rapid response to a spike in a contaminant level while the slower responding counter electrode is still producing a 'clean' gas response due to the slower response time, allowing for the slower responding counter electrode to function as a reference electrode.

In some embodiments, different working electrodes among the plurality of cells or sensing elements can be configured or otherwise adapted to monitor for different contaminants, such as at least one of ammonia, carbon monoxide, carbon dioxide, formaldehyde, formic acid, a hydrocarbon (for example methane, ethane, ethylene, or propane), or water; for example, at least one of CO, $H_2S$, $NH_3$, or acetaldehyde. The hydrogen monitoring system can detect contaminant levels of greater than or equal to 100 parts per billion (ppb) of contaminant, or greater than or equal to 1 parts per million (ppm) of contaminant, or 2 to 10,000 ppm, based on the total weight of the gas.

For example, if $H_2S$ and CO are present simultaneously in the hydrogen, the rapid uptake of CO on the electrode surface can hinder absorption of $H_2S$ (typically at lower concentrations), so initially the electrochemical active area responds to CO. However, as time goes on, $H_2S$ absorbs (in some cases irreversibly) onto the catalyst surface and a significant decrease in the current output is seen, as $H_2S$ has a much higher equilibrium surface coverage compared to CO. Therefore, a single sensing element would only detect the presence of CO (if any) and would take very long times before it detects the $H_2S$. With multiple electrochemical cell sensing elements, this can be avoided by maintaining one of the elements at a higher potential (e.g. <0.6 volts (V) RHE) to enable rapid oxidation of CO but not so high as to oxidize any absorbed S species, which typically requires >1.4 V RHE. Thus, absorption of S can be achieved without competing with CO. Another sensing element can be maintained at a lower potential (e.g. 0 to 0.3 V) where CO absorbs on the surface and affects the current response to sense for CO. Combining these two outputs, one can detect presence of CO and $H_2S$ simultaneously. This example can be extended to other contaminants, for example, $NH_3$, where the uptake into the electrolyte affects the conductivity. One electrode can be operated such that it reports the change in the conductivity of the electrolyte to detect the presence of contaminants such as $NH_3$ or foreign cation containing species.

In some embodiments, the hydrogen contaminant detector further includes an electrochemically inactive surface or material configured to detect or measure a parameter associated with the hydrogen being monitored or delivered (e.g., temperature pressure, electrical resistance, thermal resistance, etc.). For example, a thermocouple or a resistance temperature detector can be readily incorporated into the sensor configuration of FIGS. 2 and 3 as an extra set of cylindrical layers radially outward from the electrochemical cell components or additional conductors within the insulating layers. Similarly, a resistance heater can also be included as an extra cylindrical layer.

Figure 5:
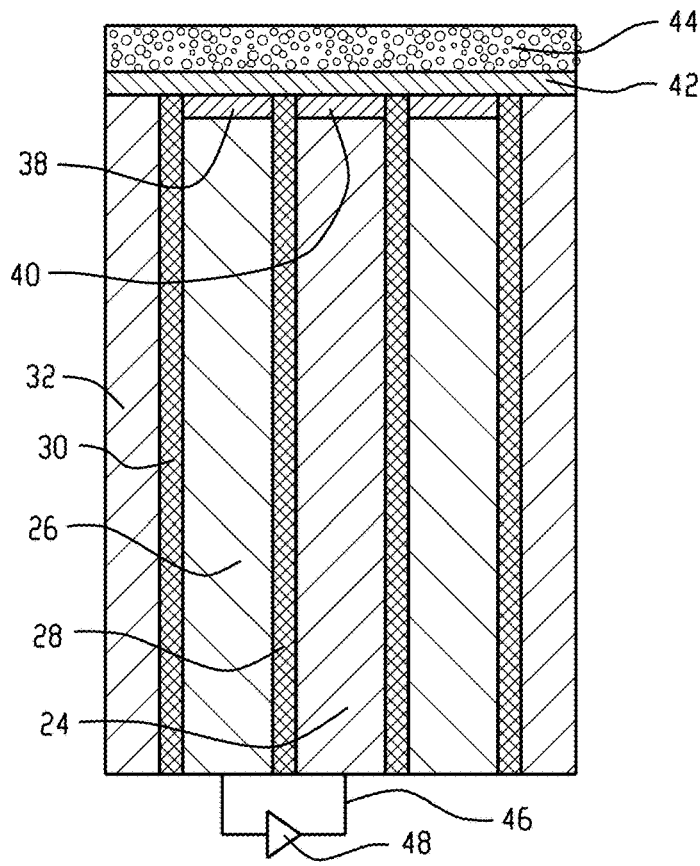
FIG. 5 is a schematic depiction of an example embodiment of an electrical circuit for a sensing element.

An example embodiment of an electrical circuit for generating and processing an electrical signal is schematically shown in FIG. 5. As shown in FIG. 5, an electrical circuit 46 connects the working electrode 24 and the counter electrode 26. Electrical circuit 46 includes a monitoring or control device 48, such as a potentiostat, which can optionally be integrated with a controller such as a microprocessor. When an impurity is introduced it can be adsorbed onto the electrode causing a reduction in the active electrode active area, which can cause a change in the electrical signal, for example, a reduction in the amount current flowing between the electrodes. The electrical signal can be obtained through various control techniques including but not limited to cyclic voltammetry (CV), polarization curve (VI), linear sweep voltammetry (LSV), constant current or constant potential hold, current pulsing or voltage pulsing or electrochemical impedance spectrometry (EIS), and digitally processed using various signal processing techniques. The hydrogen monitoring system can be operated at a constant hold of a specified voltage that can be dependent upon the impurity being measured and a change in the current can be monitored. In some embodiments, a cell or sensing element can be placed into various alternative operation modes for various purposes such as sensor regeneration or recalibration. Such modes can include, but are not limited to current reversal so that the working electrode 24 is temporarily operated as a counter electrode and a counter electrode 26 (or 34) is temporarily operated as a working electrode, voltage cycling, holds at high current levels, hydrogen evolution, inert gas purges, temperature variations, and combinations thereof.

Figure 6:
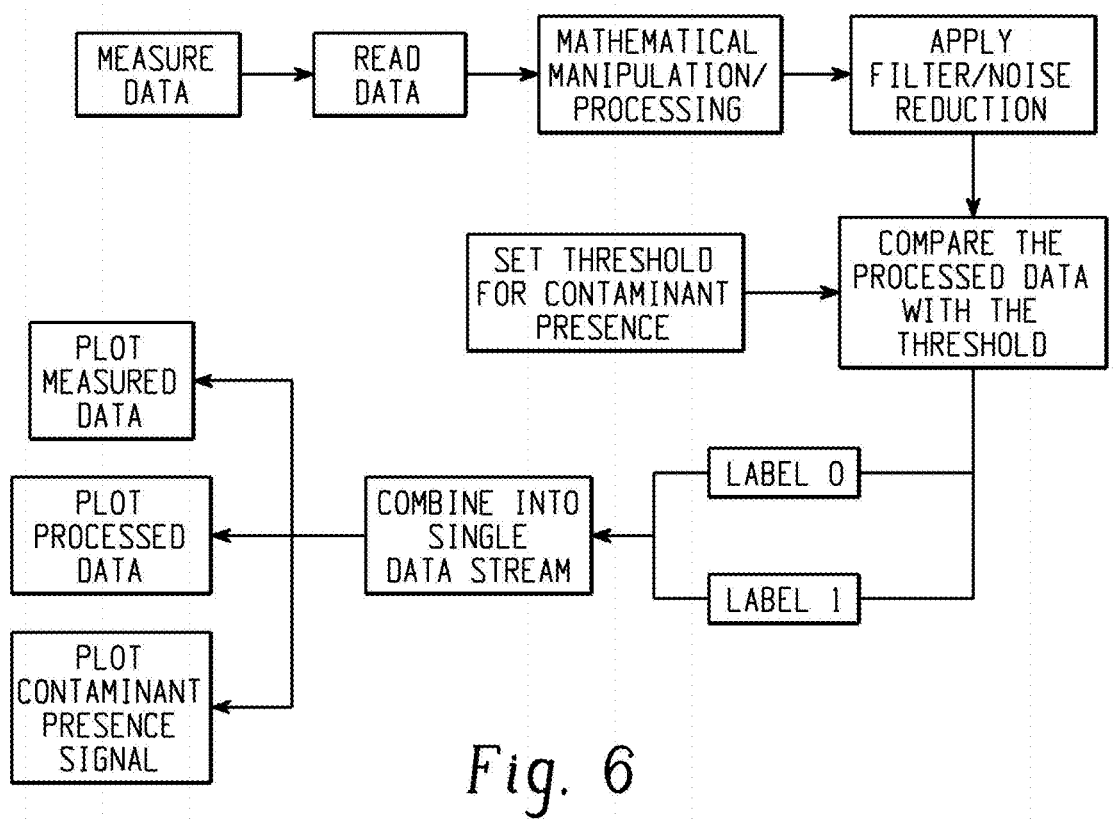
FIG. 6 is a schematic depiction of an example embodiment of a signal processing protocol.

In many cases, the current response obtained from testing $H_2$ can show a clear indication of the presence of a contaminant, however, in some embodiments an objective mathematical processing of the data can be used for a deterministic decision. In some embodiments, the deterministic decision can be a yes/no or go/no-go or a proceed/shut off decision in response to, for example, a customer-generated or system-generated demand signal in a hydrogen dispensing/delivery system. FIG. 6 schematically shows an example embodiment of a method of signal processing that generates such a yes/no signal.

The process shown in FIG. 6 can be implemented on either commercial software (e.g. MATLAB) running on a PC or with a custom software and hardware, both of which can also control the data acquisition and measurement. The data can be measured and read into the software, and mathematically manipulated, for example, by calculating at least one of the first time derivative, transforming the data (for example, by taking a Fourier transform), or by integrating. One or both of a filter (for example, a Butterworth low pass filter) or a noise reduction algorithm can optionally be applied to the manipulated date. The manipulated data can then be compared to a pre-determined contaminant presence threshold. If the threshold is exceeded, then it is determined that the fuel contains contaminants beyond allowable levels and if it is less than or equal to the threshold, then it is determined that the fuel contains acceptable levels of contaminant. Either way, a decision label, for example, 0 for allowable levels and 1 for unacceptable levels can be provided. The resulting decision label with the underlying data can then be combined into a single data stream and output for user review, for example, by providing a plot. If a decision label signifies that the impurity level is greater than a shutdown level, then the decision label can automatically trigger a shutdown response, for example, of a fueling station. This automatic shutdown ability can be critical to the success in fuel cell operations; as unknowingly utilizing a contaminated hydrogen gas can result in irreparable damage to a fuel cell. A decision label can be formulated in less than 2 minutes, or 10 seconds to 1.5 minutes from the time of the introduction of a contaminant to the hydrogen monitoring system.

A specific example of the process of FIG. 6 comprise using MATLAB software running on a PC, which can also control a potentiostat, or can easily be performed on an on-board microprocessor due to the simplicity of the components. The data can be first read into the software, and the time derivative (dI/dt) can be calculated. The change of the current response with time (dI/dt) can be a strong indicator of the trend of the current response and can strongly depend on the hydrogen composition. Utilization of the derivative can also address many of the repeatability issues between sensors or due to sensor degradation. A Butterworth low pass filter (Butterworth, 1930) can be applied to the dI/dt data, which can result in a flat frequency response. This data can be compared against a predetermined threshold value. For the examples below, the threshold was set at −0.1 microamps per minute (µA/min), and if the change in the current was found to be higher than this value, it was determined that $H_2$ contains contaminant (CO) above the threshold level. The resulting decision label along with the underlying plot data can then be combined into a single signal and provided as output.

The hydrogen monitoring system can be installed at various locations throughout a hydrogen fueling infrastructure, for example, at one or more locations including but not limited to downstream of a reformer, downstream of an electrolyzer, upstream of a compressor, upstream of a storage unit, upstream of a chiller, or upstream of fueling nozzle.

The hydrogen monitoring system can be cleaned intermittently in order to obtain optimal operation. The cleaning can comprise raising each sensing element to an elevated voltage that can be determined based on the contaminant being cleaned; and holding the sensing element at this elevated voltage for an amount of time to allow for the contaminate to desorb from the sensing element. The amount of time can be 0.5 to 5 minutes, or 1 to 3 minutes. For example, if the contaminant comprises carbon monoxide, then the carbon monoxide can be desorbed by increasing the voltage to 750 to 850 millivolts (mV) and holding for 0.5 to 5 minutes.

The following examples are provided to illustrate the present disclosure. The examples are merely illustrative and are not intended to limit devices made in accordance with the disclosure to the materials, conditions, or process parameters set forth therein.

EXAMPLES

Figure 7:
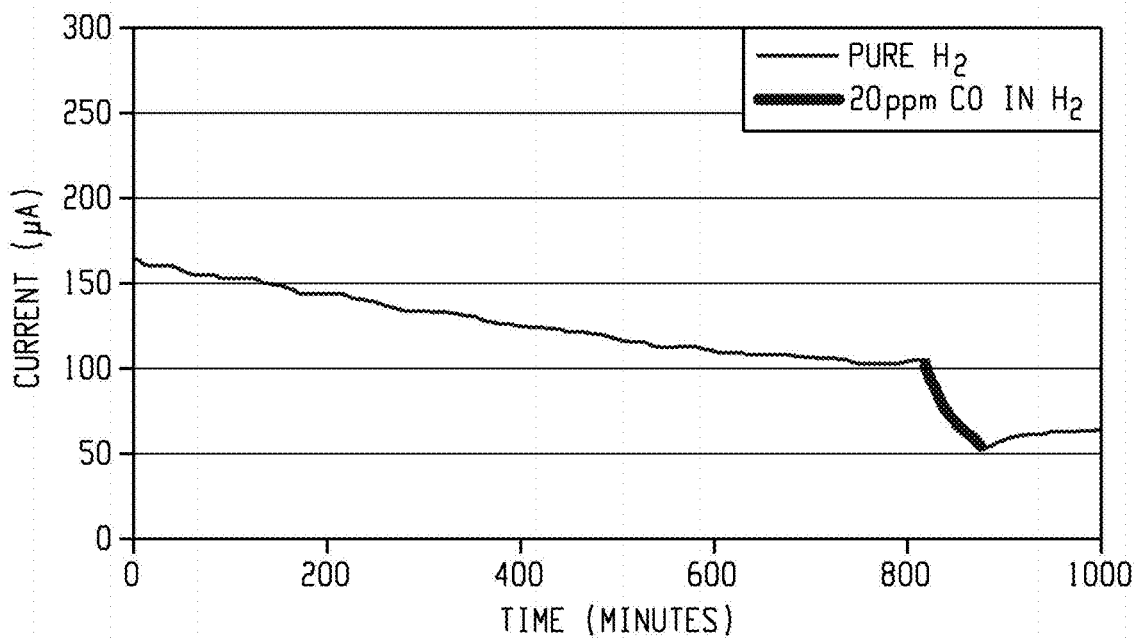
FIG. 7 is a schematic depiction of an example sensor raw signal response to 20 ppm of carbon monoxide in hydrogen.
Figure 8:
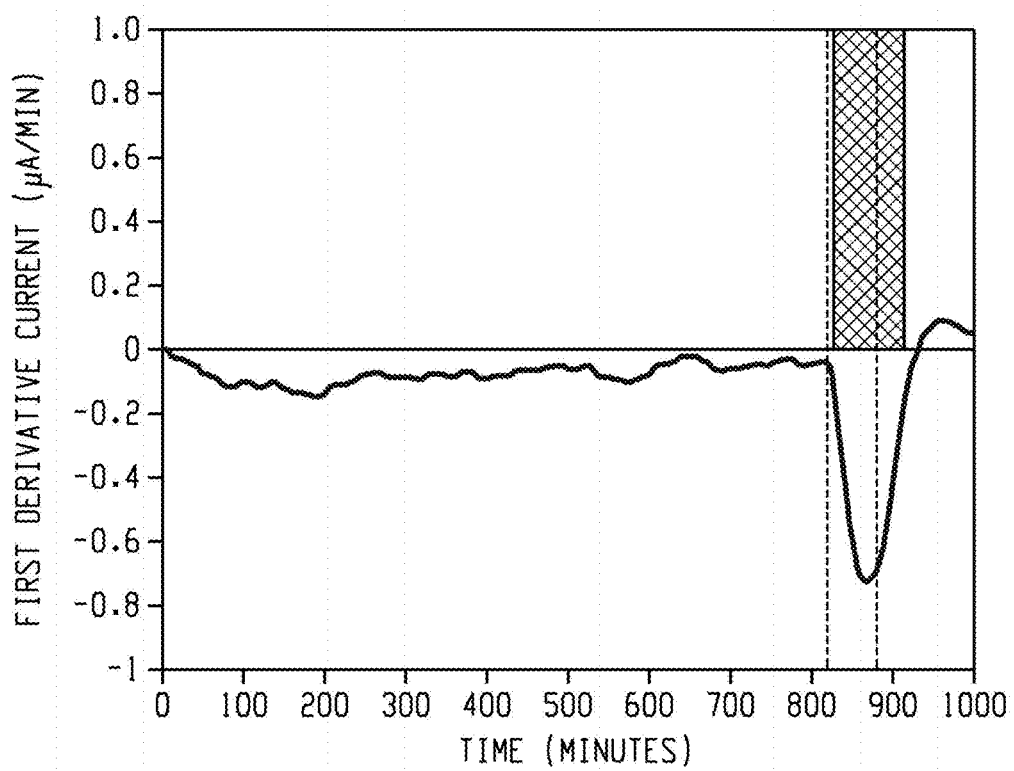
FIG. 8 is a schematic depiction of an example sensor processed signal response to 20 ppm of carbon monoxide in hydrogen.

A sensing element configured similarly to that of FIG. 2 with a thin NAFION film deposited at the tip from a 5% NAFION solution in solvent with added phosphoric acid in the electrolyte layer was exposed to a test gas of high purity hydrogen in a delivery system that can blend targeted levels of carbon monoxide at contaminant levels. FIGS. 7 and 8 show data from a sensing element tested with pure $H_2$ and $H_2$ containing 20 ppm CO. FIG. 7 shows the raw current response data, and FIG. 8 shows the trend data (dI/dt) with the Butterworth filter applied. The markings on the data related to the gas composition are calculated from the valve switching during the experiment. The shaded blocks on FIG. 8 show where the trend (dI/dt) is higher compared the preset threshold. As seen in FIG. 8, a clearly discernible and rapid response was produced to the CO contaminant.

Figure 9:
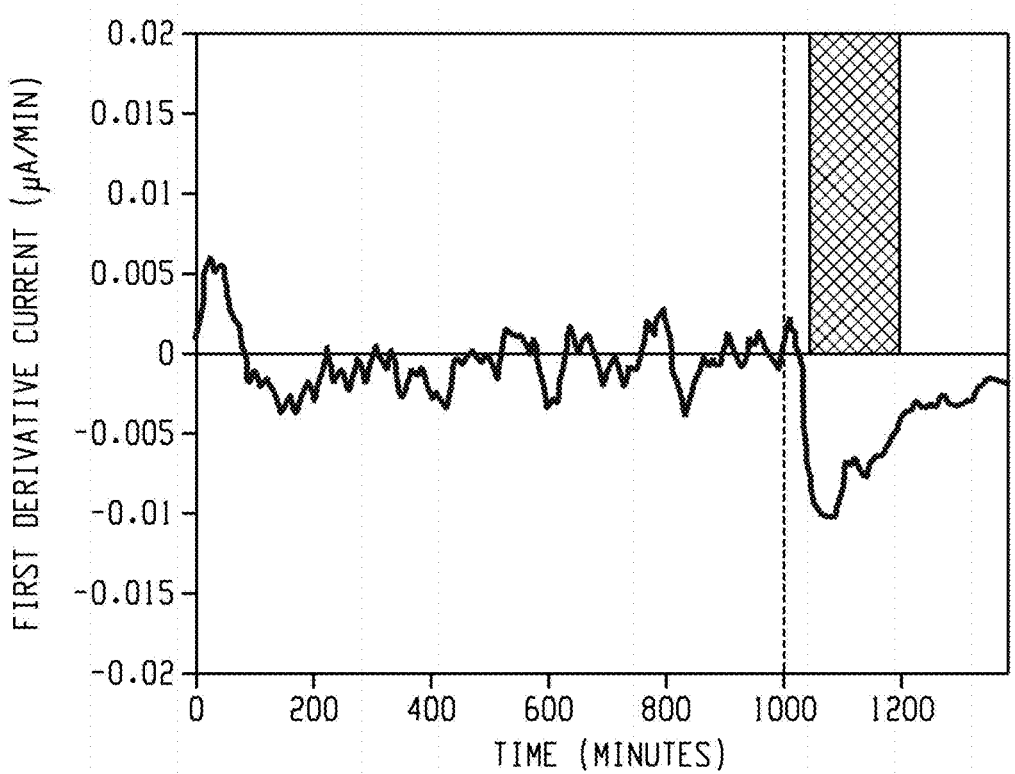
FIG. 9 is a schematic depiction of a sensor processed signal response to 20 ppm of carbon monoxide in hydrogen for another example sensor.
Figure 10:
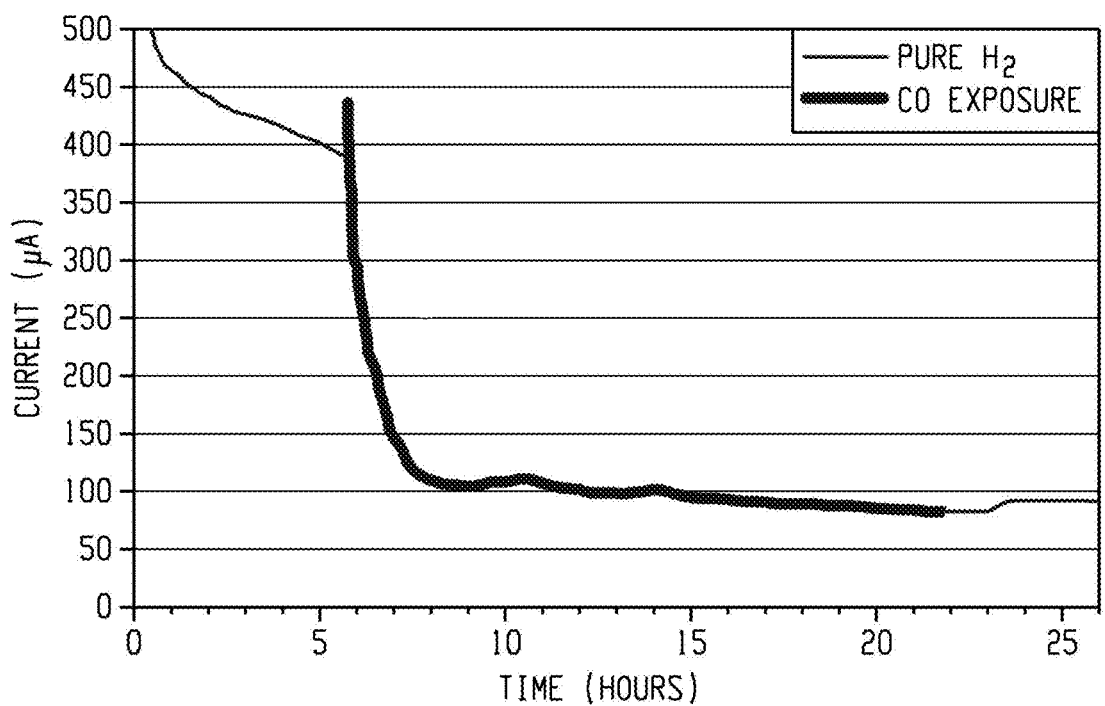
FIG. 10 is a schematic depiction of an example sensor raw signal in response to 20 ppm of carbon monoxide in hydrogen for yet another sensor.
Figure 11:
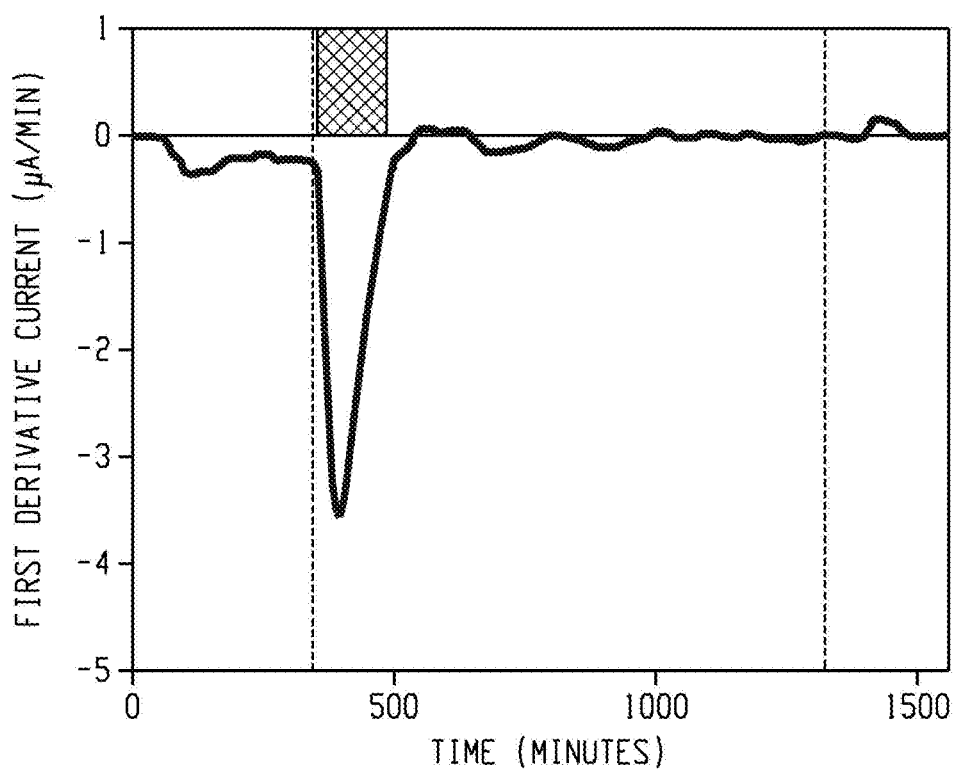
FIG. 11 is a schematic depiction of a sensor processed signal response to 20 ppm of carbon monoxide in hydrogen for the sensor of FIG. 10.

FIG. 9 shows the results of the same test protocol with a similarly constructed sensor, but with a 0.6 mil thick NAFION film deposited from a 20% NAFION solution in solvent. A clearly discernible response was produced to the CO contaminant, but with a delay of about 35 minutes between the time of introduction of the CO and producing the no signal. FIGS. 10 and 11 show the results of the same test protocol with a similarly constructed sensor, but an ion conductor formed from a 0.5 mil thick PTFE matrix imbibed with a 5% NAFION solution in solvent and evaporation of the solvent. As seen in FIG. 11, a clearly discernible and rapid response was produced to the CO contaminant.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

The terms "a" and "an" do not denote a limitation of quantity, but rather denote the presence of at least one of the referenced item. The term "or" means "and/or" unless clearly indicated otherwise by context. Reference throughout the specification to "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments. The terms "first," "second," and the like, "primary," "secondary," and the like, as used herein do not denote any order, quantity, or importance, but rather are used to distinguish one element from another.

The endpoints of all ranges directed to the same component or property are inclusive of the endpoints, are independently combinable, and include all intermediate points and ranges. For example, ranges of "up to 25 mm, or 5 to 20 mm" is inclusive of the endpoints and all intermediate values of the ranges of "5 to 25 mm," such as 10 to 23 mm, etc.

The term "combination" is inclusive of blends, mixtures, alloys, reaction products, and the like. Also, "as well as combinations of" or "at least one of" means that the list is inclusive of each element individually, as well as combinations of two or more elements of the list, and combinations of at least one element of the list with like elements not named.

Unless defined otherwise, technical and scientific terms used herein have the same meaning as is commonly understood by one of skill in the art to which this invention belongs.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While the disclosure has been described in detail in connection with only a limited number of embodiments, it should be readily understood that the disclosure is not limited to such disclosed embodiments. Rather, the disclosure, including the example embodiments disclosed herein, can be modified to incorporate any number of variations, alterations, substitutions or equivalent arrangements not heretofore described, but which are commensurate with the spirit and scope of the hereof. Additionally, while various embodiments of the invention have been described, it is to be understood that aspects of the invention may include only some of the described embodiments.

What is claimed is:

1. A hydrogen monitoring system comprising a plurality of sensing elements that individually comprise
a working electrode,
a counter electrode,
an insulating layer located in between the working electrode and the counter electrode,
a catalyst located on a distal end of both the working electrode and the counter electrode,
an electrolyte located on the end of the sensing elements on both the working electrode and the counter electrode, between the working electrode and the counter electrode, and in contact with the catalyst, and
an electrical circuit located on an opposite end of the sensing element that connects the working electrode and the counter electrode,
wherein at least some of the sensing elements are cylindrical sensing elements, wherein the working electrode and the counter electrode of the cylindrical sensing elements are concentrically located with respect to each other, wherein the working electrode and the counter electrode form a first sensing cell,
wherein the monitoring system further comprises
a second sensing cell, wherein the second sensing cell comprises a second working electrode and a second counter electrode concentrically located around both the working electrode and the counter electrode, wherein a second insulating layer is located in between the second working electrode and the second counter electrode, wherein a third insulating layer is located in between the first sensing cell and the second sensing cell, or
a second working electrode concentrically located around both the working electrode and the counter electrode, wherein a second insulating layer is located in between the second working electrode and the first sensing cell, wherein the working electrode and the second working electrode are both in electrical connection with the counter electrode via the electrical circuit.

2. The monitoring system of claim 1, comprising the second sensing cell and the second working electrode.

3. The monitoring system of claim 1, wherein one of the working electrode and the counter electrode defines a central portion of the cylindrical sensing element and the other of the working electrode and the counter electrode defines a concentric electrode portion, wherein the insulating layer is located in between the central portion and the concentric portion.

4. The monitoring system of claim 3, wherein at least one of the central portion has a diameter of 10 micrometers to 1 mm, the concentric electrode portion has a thickness of 10 micrometers to 1 mm, or the insulating layer has a thickness of 10 micrometers to 5 millimeters.

5. The monitoring system of claim 1, further comprising the second sensing.

6. The monitoring system of claim 1, further comprising the second working electrode.

7. The monitoring system of claim 1, wherein the working electrode and the counter electrode each independently comprise at least one of gold, platinum, copper, platinum, rhodium, or silver.

8. The monitoring system of claim 1, wherein the catalyst comprises at least one of platinum, palladium, rhodium, carbon, gold, tantalum, tungsten, ruthenium, iridium, titanium, or osmium.

9. The monitoring system of claim 1, wherein the electrolyte comprises at least one of perchloric acid, phosphoric acid, an acid gel, an ionic liquid, or an ion-conducting polymer.

10. The monitoring system of claim 1, wherein the insulating layer comprises at least one of magnesium oxide, aluminum oxide, silicon oxide, or zinc oxide.

11. The monitoring system of claim 1, further comprising an outer sheath.

12. The monitoring system of claim 1, further comprising a thermocouple.

13. The monitoring system of claim 1, further comprising a housing capable of withstanding an internal pressure of up to 15,000 psi.

14. A hydrogen delivery system comprising a hydrogen source, an inlet fluid flow path from the hydrogen source to the hydrogen monitoring system of claim 1, and an outlet fluid flow path from the hydrogen monitoring system to an outlet.

15. The hydrogen delivery system of claim 14, wherein the hydrogen delivery system is capable of monitoring a contaminant level of at least one of ammonia, carbon monoxide, carbon dioxide, formaldehyde, formic acid, a hydrocarbon, or water.

16. A method of determining a level of a contaminant in a hydrogen gas using the hydrogen delivery system of claim 14, comprising:
flowing the hydrogen gas from the hydrogen source along the inlet fluid flow path, past the plurality of sensing elements, and along the outlet fluid path to the outlet;
measuring data obtained from the electrical circuit and reading the data via a software program;
manipulating the data to provide a manipulated data;
comparing the manipulated data to a pre-determined contaminant threshold;
determining if the manipulated data is greater than, less than, or equal to the pre-determined contaminant threshold and providing a decision label based on the determining; and
providing an output data comprising the decision label.

17. The method of claim 16, wherein the manipulating the data comprises calculating at least one of a first time derivative of the data, transforming the data, or by integrating the data.

18. The method of claim 16, further comprising the applying a filter or a noise reduction algorithm.

19. The method of claim 16, further comprising cleaning the contaminant from the plurality of the sensing elements.

20. A hydrogen monitoring system comprising a plurality of sensing elements that individually comprise
a working electrode,
a counter electrode,
an insulating layer located in between the working electrode and the counter electrode,
a catalyst located on a distal end of both the working electrode and the counter electrode,
an electrolyte located on the end of the sensing elements on both the working electrode and the counter electrode, between the working electrode and the counter electrode, and in contact with the catalyst,
a glass frit located on a surface of the electrolyte opposite the catalyst, and an electrical circuit located on an opposite end of the sensing element that connects the working electrode and the counter electrode.

* * * * *